US009738594B2

(12) United States Patent
Doppen et al.

(10) Patent No.: US 9,738,594 B2
(45) Date of Patent: Aug. 22, 2017

(54) CRYSTALLINE PARTICLES OF SALTS OF GLUTAMIC ACID N,N-DIACETIC ACID

(71) Applicant: Akzo Nobel Chemicals International B.V., Amersfoort (NL)

(72) Inventors: Roy Gérard Doppen, Deventer (NL); Martin Heus, Arnhem (NL); Cornelis Elizabeth Johannus Van Lare, Wijchen (NL)

(73) Assignee: AKZO NOBEL CHEMICALS INTERNATIONAL B.V., Arnheim (NL)

( * ) Notice: Subject to any disclaimer, the term of this patent is extended or adjusted under 35 U.S.C. 154(b) by 64 days.

(21) Appl. No.: 14/649,361

(22) PCT Filed: Dec. 12, 2013

(86) PCT No.: PCT/EP2013/076372
§ 371 (c)(1),
(2) Date: Jun. 3, 2015

(87) PCT Pub. No.: WO2014/090943
PCT Pub. Date: Jun. 19, 2014

(65) Prior Publication Data
US 2015/0353475 A1 Dec. 10, 2015

Related U.S. Application Data

(60) Provisional application No. 61/751,398, filed on Jan. 11, 2013.

(30) Foreign Application Priority Data

Dec. 14, 2012 (EP) .................................... 12197178

(51) Int. Cl.
 C07C 227/42 (2006.01)
 C07C 229/24 (2006.01)
 C07C 229/76 (2006.01)
 C11D 3/33 (2006.01)

(52) U.S. Cl.
 CPC .......... *C07C 229/76* (2013.01); *C07C 227/42* (2013.01); *C07C 229/24* (2013.01); *C11D 3/33* (2013.01); *C07B 2200/13* (2013.01)

(58) Field of Classification Search
 CPC ... C07C 227/42; C07C 229/24; C07C 229/76; C11D 3/33; C07B 2200/13
 See application file for complete search history.

(56) References Cited

U.S. PATENT DOCUMENTS

| 5,981,798 A | 11/1999 | Schönherr et al. |
| 6,265,371 B1 * | 7/2001 | Hagino .................... C11D 3/06 510/276 |
| 2008/0194873 A1 | 8/2008 | Oftring et al. |
| 2012/0046491 A1 | 2/2012 | Mrzena et al. |
| 2012/0149936 A1 | 6/2012 | Baranyai |
| 2012/0252708 A1 | 10/2012 | Van Lare et al. |
| 2015/0321995 A1 | 11/2015 | Van Lare et al. |

FOREIGN PATENT DOCUMENTS

| DE | 4211713 A1 | 10/1993 |
| EP | 0591934 A1 | 4/1994 |
| EP | 0845456 A2 | 6/1998 |
| EP | 0884381 A1 | 12/1998 |
| EP | 1004571 A1 | 5/2000 |
| GB | 1439518 | 6/1976 |
| JP | H07-242607 A | 9/1995 |
| JP | H10-077253 A | 3/1998 |
| JP | H11-043689 A | 2/1999 |
| JP | H11-246497 A | 9/1999 |
| JP | 2002-088037 A | 3/2002 |
| JP | 2002-356464 A | 12/2002 |
| JP | 2004-359700 A | 12/2004 |
| WO | 2008/065109 A1 | 6/2008 |
| WO | 2009/024519 A1 | 2/2009 |
| WO | 2010/076291 A1 | 7/2010 |
| WO | 2011/076769 A1 | 6/2011 |
| WO | 2011/079940 A1 | 7/2011 |
| WO | 2011/146582 A1 | 11/2011 |
| WO | 2012/000915 A1 | 1/2012 |

OTHER PUBLICATIONS

International Search Report and Written Opinion for PCT/EP2013/076372, date of mailing May 9, 2014.
European Search Report for EP12197178.2, dated May 13, 2014.
Dissolvine GL Technical Brochure, Apr. 2010 (Apr. 2010), pp. 1-16, XP055058393.

* cited by examiner

*Primary Examiner* — Paul A Zucker
*Assistant Examiner* — Mark Luderer
(74) *Attorney, Agent, or Firm* — Sandra B. Weiss (57) ABSTRACT

The invention relates to a salt of glutamic acid-N,N-diacetic acid (GLDA) of the formula $GLDA\text{-}Y_mH_n$, wherein m is equal to or more than 0.5 and lower than or equal to 2.5, n+m=4, and wherein Y is a monovalent cation that is not a proton, comprising $L\text{-}GLDA\text{-}Y_mH_n$ to $D\text{-}GLDA\text{-}Y_mH_n$ in a range between 100:0 and 50:50 (L:D), characterized in that the salt is crystalline, a process to make such crystalline salt, and to uses of such salt, such as, in particular, in detergent compositions.

15 Claims, 4 Drawing Sheets

Figure 1 XRD diffractogram of amorphous NaH$_3$-GLDA of Example 4

Figure 2 XRD diffractogram of GLDA-NaH$_3$ crystals of Example 2

Figure 3 XRD Diffractogram of GLDA-KH$_3$ crystals of Example 3

Figure 4 Moisture absorption comparison between amorphous and crystalline GLDA products

CRYSTALLINE PARTICLES OF SALTS OF GLUTAMIC ACID N,N-DIACETIC ACID

This application is a national stage filing under 35 U.S.C. §371 of PCT/EP2013/076372, filed Dec. 12, 2013, which claims priority to U.S. Provisional Patent Application No. 61/751,398 filed Jan. 11, 2013, and European Patent Application No. 12197178.2, filed Dec. 14, 2012, the contents of which are each incorporated herein by reference in their entireties.

The invention relates to crystals of salts of glutamic acid N,N-diacetic acid (abbreviated as GLDA), a chelating agent of which the acid has the formula COOH—CH(—$CH_2$—$CH_2$—COOH)—N—($CH_2$—COOH)$_2$ (also referred to as GLDA-$H_4$ in the following), to processes to produce said crystals, and to the use of such crystals.

The detergent market is currently undergoing important changes. Due to ecological and regulatory reasons the use of phosphate in high concentrations In detergent formulations is to be banned altogether or must at least be greatly reduced. The formulators of detergent products have to find alternatives to replace the phosphate compounds, with the most promising replacements being biodegradable chelating agents such as GLDA or its salts. Such chelating agents are used in a concentration from 5% to 60%. Many detergent formulations contain co-builders, which are typically polymers or phosphonates and also phosphates, silicates, and zeolites These co-builders are present in formulations in a concentration from 1% to 50%.

In powder or tablet detergent formulations, solid raw materials are required by the formulator. For example, in automatic dishwashing (ADW) applications the raw materials have to be in granule form to improve the tabletting and solids handling of the formulation. These granules typically have a size comprised between 100 and 3,000 microns. The usual form in which glutamic acid N,N-diacetic acid (GLDA) and its salts are available is a solution with an active content from 35% to 60%, After drying, the powder or granules, when obtained in the amorphous state, show extensive hygroscopic properties, which is unacceptable for the ADW formulators. Whether in powder or granule form, the amorphous chelating agent GLDA and its salts exhibit hygroscopic properties, rendering the material sticky and thus introducing storage, handling, and manufacturing problems. Flow properties of particles are critical in many ways. During manufacture of the particles themselves, they must flow smoothly relative to one another. Additionally, they must then be successfully transported to storage and transport containers. Finally, they must again be transported from storage and fed into a powder or tablet manufacturing facility. Flow problems arise due to several causes. In the case of amorphous $H_4$GLDA and its salts poor flow will be caused by moisture pick-up, resulting in a wet sticky product that will form lumps.

GLDA and its salts will definitely move into the ADW market and likely into many other fields where a strong, green chelate is needed. The term "green" here denotes materials with a high renewable carbon content, a sustainable environmentally friendly production process, and a positive biodegradability assessment. While the state of the art builders used in detergent formulations, such as sodium tripolyphosphate (STPP) and nitrilo triacetic acid (NTA), are isolatable as dry particles, the hygroscopic, dusty, and sticky properties of solid amorphous GLDA are disadvantageous and make co-granulation or coating necessary, so it would be highly desirable to improve the non-hygroscopic properties of GLDA and its salts. WO2011/076769 for example discloses coating particles of amorphous GLDA-$H_4$ or one of its salts to improve the hygroscopic properties.

US20120046491 discloses the preparation of a powder comprising one or more derivatives of glutamine-N,N-diacetic acid or glycine-N,N-diacetic acid with a degree of crystallinity of ≥30%, the process comprising concentrating an aqueous solution to obtain a crystal slurry, wherein one concentration range is from 20% to 60% by weight (starting material), based on the total weight of the crystal slurry, and ripening the crystal slurry in a paste bunker and then in a thin-film contact dryer, wherein the residence time in the paste bunker (seeds: fine powder up to 50% of total weight) and in the thin-film contact dryer is in total ≥15 min and the concentration occurs in an evaporator with rotating internals which are arranged at a distance relative to an inside wall of the evaporator of ≤1% of a diameter of the evaporator (high shear rate in the liquid film on the inside wall). Temperature ranges for the first process step are between 50° C.-140° C. and preferably between 80° C.-110° C., and pressure ranges are between 0.1 and 4 bar, preferably between 0.8 and 1.2 bar. Ripening is carried out for at least 15 minutes and up to 3 hours and thin-film treatment is carried out for between 0.5 minutes and 20 minutes from 60° C. up to 140° C. A powder is obtained which predominantly has the crystal modification of the monohydrate or the dihydrate of MGDA (methylglycine N,N-diacetic acid). The complicated process appears to be specifically designed for MGDA and is not reproducible for GLDA or its salts, in particular since the temperature ranges of the process are too high for the crystallization of GLDA or its salts.

US20120149936 discloses a process for preparing crystalline solids of glycine-N,N-diacetic acid derivatives of sufficiently low hygroscopicity by introducing one crystalline compound as a seed, and a spray granulation is carried out, which may be followed by a heat treatment step to increase the crystallinity. Only glycine-N,N-diacetic acid derivatives are mentioned in the document and, again, the temperatures are too high for the crystallization of GLDA.

EP 845 456 discloses the preparation of a crystalline solid of a glycine N—N-diacetic acid derivative. In the Examples a concentrated solution of the trisodium salt of MGDA (methylglycine N,N-diacetic acid) is crystallized using seeds as crystallization initiator. However, this process is not reproducible for GLDA and its salts, as the same will not crystallize. GLDA and in particular its salts become extremely viscous at high concentrations and crystallization will not occur.

DE 42 11 713 discloses a process to prepare the chelating agents GLDA and ASDA (aspartic acid N,N-diacetic acid). Though it is suggested in general that the materials could be isolated by several methods, one of which is crystallization, all the examples deal with depositing ASDA in the amorphous form.

EP 1004571 discloses a process to prepare an aqueous solution of GLDA and the crystallization of the ammonium ferric salt thereof. This patent makes use of the completely changed properties of a metal chelate in comparison to a chelating agent without a metal ion being chelated. For those skilled in the art it is known that metal GLDA complexes have reduced solubility in comparison with the empty ligand.

JP2002356464 discloses a process to prepare highly pure (salt-free) solutions of chelating agents and suggests crystallizing them in the acidic form and subsequently dissolving them in an aqueous solution. However, the preparation of a highly pure GLDA solution is done by converting a solution of GLDA to an acidic form using an ion exchange resin and then adjusting the pH to the right value by the addition of an amine. No solid materials are disclosed or exemplified.

A few documents seem to disclose the preparation of GLDA, EP-A-0 591 934 in Synthesis Example 2 and EP-A-0 884 381 in Synthesis Example 1. A Japanese patent application, JP 11 043689, discloses the same synthesis for GLDA as EP-A-0 884 381. However, EP-A-0 591 934 in the Example has a pH that would be high enough to prepare GLDA salt, while in EP-A-0 884 381 the pH is so low that if it leads to anything, it will be a GLDA-$H_n$ solid wherein n is higher than 3.5. In addition, the procedures from EP-A-0 591 934 and EP-A-0 884 381 when reworked were found to not give any crystals of GLDA.

Several documents disclose the crystallization of chelating agents (also often referred to as aminopolycarboxylic acids). Thus JP 2002088037, JP 07242607, JP 2004359700 mention or disclose the crystallization of a number of amino acid diacetic acids. None of these documents relates to GLDA, nor to crystallization of salts of GLDA.

JP 1998/077253A discloses the preparation of an aminodicarboxylic acid N,N-diacetic acid by crystallization in a solution of a pH of about 2 and addition of methanol. Where this process is repeated for GLDA, the document speaks of solid GLDA instead of crystalline GLDA and no disclosure or evidence is shown (e.g. in the form of XRD or DSC results) that the material produced is crystalline.

The disadvantage of the prior art is that the processes disclosed for MGDA and other chelating agents, apart from being complex, do not work for GLDA or produces solid yet amorphous material. The prior art does not disclose a process to produce crystalline salts of GLDA.

As described above, solid amorphous GLDA (available as commercial product) has the disadvantage of being hygroscopic.

Therefore, less hygroscopic GLDA chelating agents are needed which show improved storage, handling, transport, and flowing properties.

Further, because chelating agents are used frequently in detergents which are to a large extent neutral or alkaline, there is a need for GLDA chelating agents which have a not too acidic pH. In the case of partial salts of GLDA, if needed at all, only limited amounts of an alkaline product (like a bicarbonate or sodium carbonate) will need to be added to increase the pH to 6 or higher without increasing the total volume too much.

Quite surprisingly, it has been found possible to isolate salts of GLDA of the formula GLDA-$Y_mH_n$, wherein m on average is equal to or more than 0.5 and lower than or equal to 2.5, n+m=4, Y is a monovalent cation that is not a proton, in the form of crystals.

This holds even more since it has been found that making a crystalline particle of a salt of GLDA (wherein GLDA is in the form of the tetra-anion, looking at the formula COOX—CH(—CH$_2$—CH$_2$—COOX)—N—(CH$_2$—COOX)$_2$, wherein not each X is a hydrogen atom but instead a cation, preferably alkali metal) is by no means a straightforward process when applying commonly known techniques such as anti-solvent crystallization and salting-out processes.

Accordingly, the present invention provides salts of glutamic acid-N,N-diacetic acid (GLDA) of the formula GLDA-$Y_mH_n$, wherein m on average is equal to or more than 0.5 and lower than or equal to 2.5, n+m=4, Y is a monovalent cation that is not a proton, comprising L-GLDA-$Y_mH_n$ to D-GLDA-$Y_mH_n$ in a range between 100:0 and 50:50 (L:D), wherein the salt is crystalline. These crystalline salts show a reduced hygroscopic behaviour compared to the equivalent amorphous particles and are biodegradable.

Figure 1:
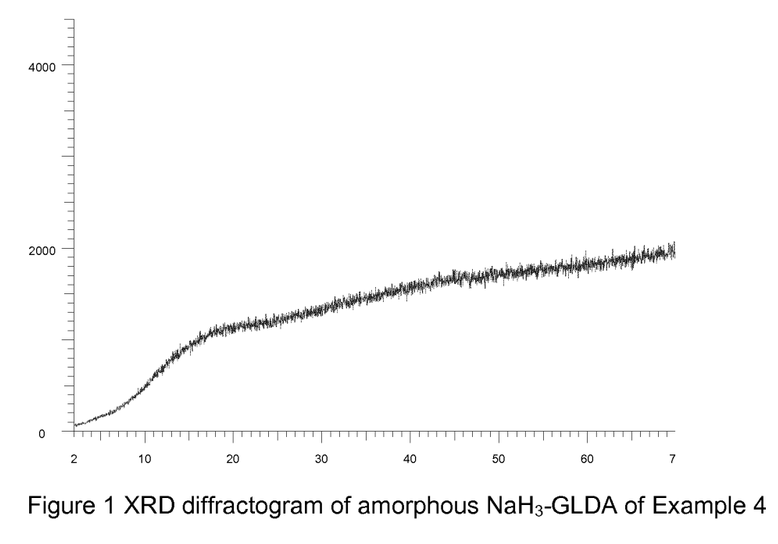
FIG. 1 is an x-ray diffraction diffractogram of the amorphous NaH$_3$-GLDA prepared in Example 4.

According to this invention, a solid compound is crystalline when it has a three-dimensional periodic structure (crystal). A three-dimensional periodic structure is different from an amorphous structure in that it shows interference in monochromatic X-ray diffraction which fulfills the Bragg equation (2 d sin Θ=n λ), whereas amorphous materials produce a broad background signal (FIG. 1). The crystalline salt of the present invention further exhibits reduced hygroscopicity compared to amorphous salts of GLDA of the formula GLDA-$Y_mH_n$.

In a preferred embodiment, the cation Y is an alkali metal. In another preferred embodiment, m is between 0.5 and 1.5 and n is between 2.5 and 3.5, more preferably m is about 1 and n is about 3. In an even more preferred embodiment, the crystalline salt of GLDA is GLDA-NaH$_3$, or GLDA-KH$_3$, or GLDA-LiH$_3$.

The biodegradable crystalline salts of the invention comprise L-GLDA-$Y_mH_n$ to D-GLDA-$Y_mH_n$ in a range between 100:0 and 50:50 (L:D), i.e. it was found that in order to be able to obtain crystals, the GLDA needs to be at least partially racemized. The salt preferably comprises L-GLDA-$Y_mH_n$:D-GLDA-$Y_mH_n$ between 75:25 and 50:50, even more preferably L-GLDA-$Y_mH_n$ to D-GLDA-$Y_mH_n$ as an (about) 50:50 mixture of equal quantities of the two enantiomers L-GLDA-$Y_mH_n$ and D-GLDA-$Y_mH_n$, i.e. the product is a racemic mixture of (more or less) equal quantities of the two enantiomers of GLDA, wherein the (partially) racemized products are readily biodegradable as optically pure (L-) product. Each enantiomer rotates the plane of polarization of plane-polarized light through a characteristic angle, but because the rotatory effect of each component exactly cancels that of the other, the 50:50 racemic mixture is optically inactive.

The crystalline particles of the invention in one embodiment have a particle size of 20 to 3,000 microns (μm), preferably of 500 to 2,000 microns, most preferably between 50 and 300 microns.

The disadvantage of particles which are too small is that the obtained product is e.g. dusty, which reduces manageability and also easier caking is observed. The disadvantage of particles which are too large is e.g. that these particles take longer to dissolve, which make them less suitable for detergent, such as ADW, applications.

In addition, the present invention provides a process to prepare the salts of GLDA of the formula GLDA-$Y_mH_n$, wherein m is equal to or more than 0.5 and lower than or equal to 2.5, n+m=4, and wherein Y is a monovalent cation, wherein the salt is crystalline, comprising in a first step providing an aqueous solution containing a salt of GLDA or a precursor thereof, in a second step ensuring that the pH of the aqueous solution is equal to or more than 1.8 and less than 5 and performing a racemization step, one after the other in random order, or simultaneously, and in a third step allowing the aqueous solution to crystallize.

The second step of the process comprises a racemization step, as it was found to be impossible to isolate crystals of optically pure L-GLDA-$Y_mH_n$ wherein at least 0.5 equivalent of a cation Y is present. The racemization step serves to at least partially racemize pure L-GLDA-$Y_mH_n$ into a mixture of D-GLDA-$Y_mH_n$ and L-GLDA-$Y_mH_n$. The racemization step in a preferred embodiment of the process of the present invention is a temperature treatment step. The temperature treatment step according to this invention is a temperature and time-dependent treatment which may comprise allowing the solution to stand for an extended period of time (months, easily up to more than 6 months) at room temperature. The temperature treatment step may preferably comprise heating the aqueous solution to between 90° C. and 140° C., preferably to between 98° C. and 137° C., for a shorter period of time (hours). In some embodiments, the temperature treatment step may involve an increased pressure.

It was found that if the above crystallization process is tried at pH greater than 5, GLDA will not crystallize. At the same time, it was found that if the process is performed at a pH of equal to or more than 1.8 and less than 5, crystallization is very well possible. To our surprise e.g. GLDA monosodium crystals can be isolated, which is not the case for other well-known chelating agents such as EDTA, NTA, HEDTA or DTPA, which are not suitable for many applications in which a (too) acidic pH is undesired, of which the most prominent application is in a detergent formulation. It was additionally found that GLDA crystals (in particular GLDA-$NaH_3$ and GLDA-$KH_3$) are significantly less hygroscopic when compared to amorphous GLDA salts.

Furthermore, it should be realized that acidifying chelating agents is a costly excercise, the more acidified the product, the more expensive it becomes, which makes derivatives based on GLDA acidified material more expensive also, which is undesired from an economic point of view. The present invention hence represents the best balance in terms of reducing hygroscopicity, choosing the right pH range for the crystallization process, and avoiding unnecessary costs when providing a product that is more suitable for certain applications in which a too acidic pH is unnecessary, or even undesired.

The aqueous solution of the first step may be an aqueous solution of salts of GLDA and/or of one of its precursors, in particular, an aqueous solution of GLDA-$H_4$.

The aqueous solution of the first step may be provided e.g. by dissolving a GLDA salt in water or starting from already dissolved GLDA acid or dissolving the same in water and adding a caustic, preferably NaOH and/or KOH and/or LiOH, until the desired pH is reached.

The second step in embodiments wherein the starting solution has a different pH involves a pH adjustment step, wherein the pH is adjusted to be between 1.8 and 5. Preferably, the pH of the second step is between 1.8 and 4.8.

Starting in the second step from the aqueous solution of a GLDA salt or its precursor provided in the first step, the pH of equal to or more than 1.8 and less than 5 may also be ensured by acidification using an electrolytical, e.g. Bipolar Membranes (BPM), acidification process, such as described in e.g. EP-A-1004571 or WO 2008/065109, by using ion exchangers and/or by adding an inorganic acid to the aqueous solution until the aqueous solution has a pH of equal to or more than 1.8 and less than 5. If ion exchangers are used, the aqueous solution may further be sieved in order to remove any ion exchange resin residues.

The pH in the second step of the process according to this invention is the pH of the solution when measured for a 5 wt % aqueous solution, at a temperature of 30° C. Of course this does not imply that the solution of the second step should contain 5 wt % of GLDA; as explained below, it is preferably more concentrated.

It is also possible for the second step of the process to start from GLDA acid, i.e. a solution of which the pH when measured at 5 wt % and 30° C. is lower than 1.8, and to raise the pH by adding caustic, preferably NaOH and/or KOH and/or LiOH, to the aqueous solution.

The second step may further comprise an optional concentrating step.

The concentration step may be carried out until the critical concentration of the aqueous solution, the supersaturation, is reached. The concentrating step of the process may be carried out until the aqueous solution has a concentration of more than 10 wt %, preferably equal to or more than 15 wt %, even more preferably more than 20 wt % up to or equal to 80 wt % of GLDA-$Y_mH_n$, based on the weight of the aqueous solution. When the more concentrated solutions are so viscous that an efficient crystallization becomes more difficult, the skilled person will know that reducing the viscosity thereof, for example by heating the solution, may be desirable.

In a further embodiment, the aqueous solution may be concentrated in the concentrating step by way of evaporation, optionally at an elevated temperature.

In a preferred embodiment, in the aqueous solution that is allowed to crystallize the amount of GLDA-$Y_mH_n$ is at least 15 wt % on total solution. More preferably, the amount of GLDA-$Y_mH_n$ is at least 20 wt % on total solution.

In another preferred embodiment, at least 75 wt % of the total organic compounds in the aqueous solution that is allowed to crystallize is GLDA-$Y_mH_n$. Organic compounds are defined as hydrocarbon based compounds (compounds that contain at least one covalent hydrogen-carbon bond) and include compounds that can be considered impurities formed during the preparation of GLDA such as formaldehyde, nitrilotriacetic acid, glutamic acid, glycolic acid, formic acid, or glutamic acid N-monoacetic acid (=GLMA, which can be both linear and cyclic). More preferably, at least 85 wt % on the total weight of organic compounds in the solution is GLDA-$Y_mH_n$, most preferably at least 90 wt %.

In yet another preferred embodiment, the weight amount of GLDA-$Y_mH_n$ on total inorganic compounds in the solution, i.e. the weight ratio GLDA-$Y_mH_n$: inorganic compounds, in the solution allowed to crystallize is higher than 1:1, more preferably higher than 2:1, and most preferably higher than 3:1, wherein inorganic compounds are compounds that are not organic compounds as defined above and not water. Inorganic salts are the most important examples of inorganic compounds. It was found that salting out GLDA-$Y_mH_n$ crystals is very complex and increasing the salt load merely has an inhibiting effect on the crystallization of the organic GLDA-$Y_mH_n$ compound.

In the third step of the process wherein the solution is allowed to crystallize in some embodiments the solution is allowed to stand for an extended period of time, a cooling and/or, a seeding step are performed.

Cooling may be batch controlled-cooling crystallization, e.g. using pre-determined temperature profiles.

When a seeding step is performed in the third step, the seeding may for example comprise adding dust and/or glass particles, crystals of the respective crystalline salt. Seeding may be carried out by way of macro- or micro-seeding, temperature shocks, vibration and/or providing a suitable surface for adhesion. Seeding may be carried out at elevated temperatures and/or stepwise.

The third step of the process may further be carried out by spraying the aqueous solution of the third step on seeding crystals.

To get a good yield, the third step of the process is preferably performed at a temperature of equal to or below 35° C., preferably 30° C. Preferably, during the crystallization process the solution of the GLDA-$Y_mH_n$ salt is cooled to a temperature of equal to or below 25° C. In more preferred embodiments the temperature is at least 0° C.

In a further embodiment, the process according to this invention may further comprise an optional separation step, wherein the crystalline product of the third step is separated from the mother liquor (that part of the aqueous solution which is left after crystallization).

The process according to this invention may optionally comprise a drying step in which the crystalline salt of GLDA of the formula GLDA-$Y_mH_n$ is dried. Drying may be conducted at elevated temperatures and/or under reduced pressure, preferably vacuum.

The process according to this invention can be carried out as a continuous process, e.g. by using resulting products as seeds in the third step. Crystallization may also be induced repeatedly in the separated mother liquor.

In a further embodiment it is possible to add carbonates/bicarbonates and/or silicates to the resulting product of the third step, so that the pH of an aqueous solution of the resulting product is above 6. In one embodiment the crystals are mixed, co-granulated or coated with a sufficient quantity of carbonates and/or silicates. Most preferably, the carbonates and/or silicates are sodium based.

The invention also provides the use of the crystalline salt of GLDA-$Y_mH_n$ of the invention in detergents, agriculture, in oil field applications, feedstock applications, pharmaceutical applications, in water treatment, and other applications that require or profit from the benefits provided by this invention, i.e. the sequestration of metal ions which can otherwise lead to precipitation, low hygroscopicity, inhibition or dissolution of scale growth and pH. One preferred embodiment of this invention is the use of the particles in automatic dish washing formulations. Another preferred embodiment of this invention is the use of the particles in oil well completion and production operations.

The crystalline salts of GLDA-$Y_mH_n$ are an excellent feedstock to produce metal-GLDA products, as their sufficiently low pH after dissolution allows reaction with metal oxides/metal hydroxides at sufficient speed and under mild conditions, so avoiding the need for the more expensive metal salts while having as an additional advantage that they introduce only a limited amount of a cation Y-containing salt, such as e.g. a sodium or potassium salt, into the aqueous metal-GLDA solution.

The invention additionally relates to detergent compositions containing a crystalline salt of GLDA-$Y_mH_n$ of the present invention and further comprising at least one component selected from the group of cleaning additives, anti-scaling additives, builders, protective colloids, chelating agents, surfactants, corrosion inhibitors, and inorganic or organic acids.

The invention additionally relates to pharmaceutical preparations containing a crystalline salt of GLDA-$Y_mH_n$, and further comprising a pharmaceutically acceptable carrier, preferably lactose derivatives and/or cellulose derivatives.

EXAMPLES

The materials used are:
Dissolvine GL-47-S (a 47 wt % solution of L-GLDA tetrasodium salt in water), ex Akzo Nobel Functional Chemicals LLC, Chicago Ill., USA.
Potassium Hydroxide, 45% Solution, AR®, ex Avantor.
Sodium Hydroxide, 50% Solution, AR®, ex Avantor
XRD Method and Equipment Used for Analysis:
The diffractograms of crystalline salts of GLDA according to this invention were recorded using a Bruker-AXS D8 reflection-diffractometer using Ni filtered Cu—$K_\alpha$ radiation. Generator settings are 40 kV, 40 mA. A graphite monochromator was used with divergence and anti-scatter slit V20 (variable 20 mm), detector slit 0.6 mm. The measuring range was 2Θ=2.0–70.0°, step size 0.02°, time per step 6.5 seconds.

The Topas software package from Bruker was used for the diffractograms.

NMR in this document is $^1$H NMR.

CZE stands for Capillary Zone Electrophorese

Example 1

Acidification of GLDA Solutions

To lower the pH of a GLDA-$Na_4$ solution, Dissolvine GL-47-S, an acidification was performed using a Bi-Polar Membranes (BPM) process. In the BPM process, a bipolar membrane electrodialysis stack was used as described in WO 2008/065109. Such a unit consists of bipolar membranes and a cation exchange membrane. The sodium cations are removed through the cationic exchange membrane, while the hydrogen is added into the product stream via an electrochemical reaction. That way the solution is gradually acidified without having residual sodium cations present. This means that a "salt-free" acidification has occurred.

The experimental set-up consisted of three vessels to recycle fluids through the BPM unit. The temperature was controlled by applying heating/cooling to the jacketed reactors. The acid reactor was a 1 l stirred glass reactor and the base and electrolyte loop both used 1.5 l glass reactors without stirring. Nitrogen was passed through the electrolyte solution via a gas sparger in order to dilute the hydrogen gas produced at the cathode to far below the explosion limit.

The reactor was charged with a ca 42 wt % GLDA-$Na_4$ solution and the recirculation of the reactor content over the BPM stack was started. Once the GLDA-solution was heated to 40° C., an electric current was applied. The voltage (V) over the stack was limited to 25V and the electric current (I) was controlled manually to a maximum of 15 A. When the desired pH was reached, the current to the BPM was minimized and both the reactor and BPM contents were collected.

The acidified GLDA solution was established to be a 44 wt % solution of GLDA having a pH of about 2.5.

Example 2

Preparation of Crystalline D,L-GLDA-$NaH_3$

The resulting 44.1 wt % L-GLDA aqueous solution with pH 2.5 (which corresponds to a solution containing about 1 equivalent of sodium cation per GLDA anion) of Example 1 were submitted to a heat treatment for 174 hours at approx. 100° C. to provide for racemization. The obtained D,L-GLDA-NaH$_3$ solution was concentrated to a 50.2 wt % (50:50) L,D-GLDA-NaH$_3$ aqueous solution in a rotavapor, water bath temperature 70° C. and reduced pressure (20 mbar).

An amount of 1,852 g of the above solution was charged to a 3 l jacketed glass reactor provided with an anchor stirrer. The aqueous solution was heated to 98° C. for full dissolution. Whilst being stirred the clear solution was seeded with GLDA-NaH$_3$ crystals and cooled to 30° C. within 15 hours.

The crystal slurry was centrifuged in a horizontal Rousselet drum centrifuge to separate the mother liquor from the crystalline product.

After separation, 1,198 g of mother liquor with a concentration of 29.3% (established by way of Fe-TSV, Iron Total Sequestering Value) and 598.6 g of wet cake were obtained. The wet cake was washed twice with a small amount of water and dried under vacuum at 40° C., yielding ~450 g of dry crystals.

Figure 2:
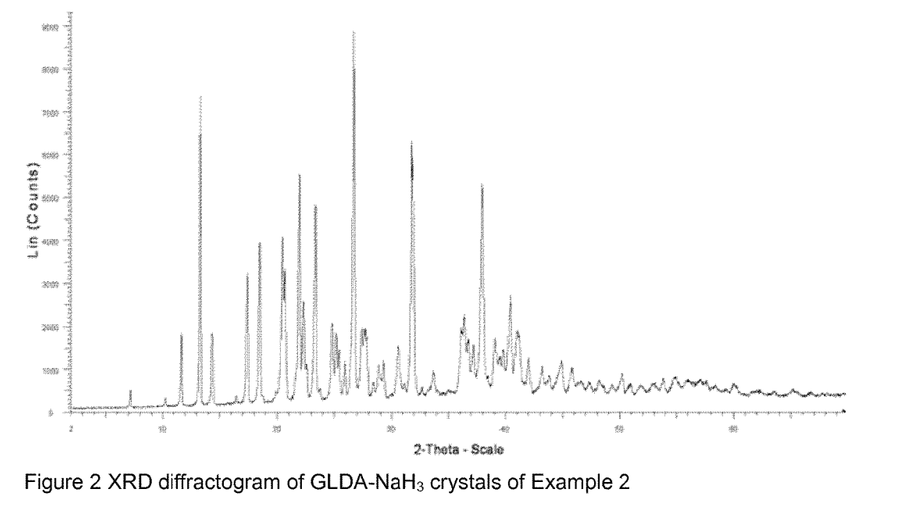
FIG. 2 is an x-ray diffraction diffractogram of the NaH$_3$-GLDA crystals prepared in Example 2.

FIG. 2 shows an XRD of the obtained crystals showing interference, fulfilling the Bragg equation.

Example 3

Preparation of D,L-GLDA-KH$_3$ 3 l of Dissolvine GL-47-S aqueous solution were acidified to obtain a 44 wt % solution of GLDA with a pH of 1.25 using the above-described BPM process but running it longer than in Example 1.

870 g of the 44 wt % L-GLDA aqueous solution with pH 1.25, which is a saturated solution at room temperature, were heated to 80° C. in a glass container until supersaturation. The aqueous solution was allowed to stand in the container for 63 days at 80° C. in an oven, allowing the concentrated aqueous solution to racemize and to crystallize. The precipitate in the mother liquor was ground and the obtained slurry was filtered applying a G3 glass filter. The wet cake was subsequently washed with ice water and dried under vacuum at ambient temperature. After drying 191.3 g of D,L-GLDA-H$_4$-crystals were obtained.

78.0 g of the D,L-GLDA-H$_4$ crystals were dispersed in 62 g demineralized water.

To the stirred slurry 37 g of KOH-45% aqueous solution were added, dissolving the crystals and reaching a pH of 2.34 as is.

To the obtained slightly turbid solution further KOH-45% aqueous solution was added to obtain a pH of 2.50 (as 1% in water). The solution was filtered using a syringe with 0.45 μm filter.

The clear solution was heated to 95° C. and allowed to cool to 50° C. and stirred overnight.

The obtained white precipitate was isolated applying a G3 glass filter. The wet cake was washed twice with a small amount of cold water and dried under vacuum at 25° C.

Figure 3:
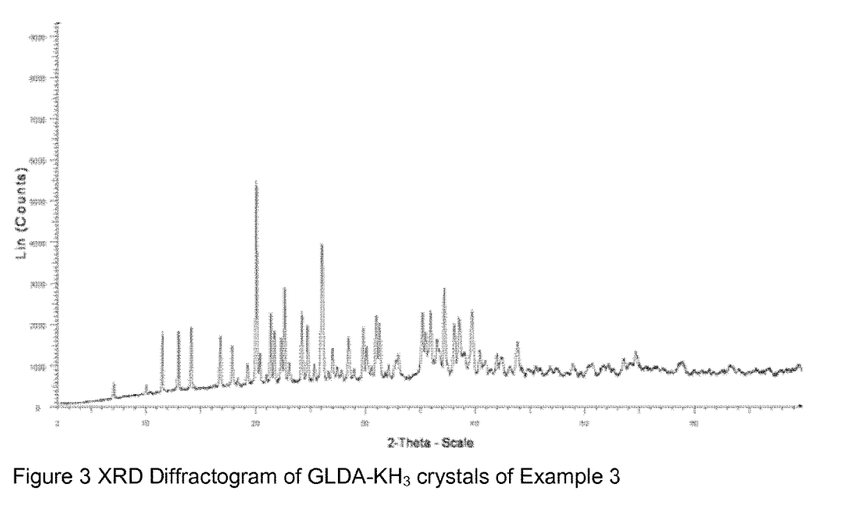
FIG. 3 is an x-ray diffraction diffractogram of the KH$_3$-GLDA crystals prepared in Example 3.

FIG. 3 shows an XRD of the obtained crystals showing interference, fulfilling the Bragg equation.

Example 4

Test of Hygroscopicity

GLDA-NaH$_3$ crystals
Dissolvine GL-47-S was acidified in a two-step process by way of ion exchange using first the ion exchange resin Duolite C-476, Rohm&Haas, 3,000 liters, and next the ion exchange resin Lewatit CNP-80, Bayer, 5,500 liters. The aqueous GLDA-NaH$_3$ solution obtained (pH 3.2 as is) was concentrated under atmospheric pressure within approx. 12 hours at an initial boiling temperature of approx. 105° C., a temperature that became 115° C. at increasing concentration.

A 40 L-reactor was pre-charged with 29.5 kg of the obtained 40.4 wt % solution having a pH of 3.2 as is.

The reactor content was stirred for 14 hours at 100° C. and concentrated to give a 60.4 wt % D,L-GLDA-NaH$_3$ solution.

The aqueous GLDA-NaH$_3$ solution was allowed to cool to 40° C. and kept at this temperature for 24 hours to allow the D,L-GLDA-NaH$_3$ to crystallize.

18.99 kg of the resulting slurry were filtered applying a G3 glass filter, yielding 7.34 kg of wet cake and 11.65 kg of mother liquor (Fe-TSV=55.9%).

The wet cake was subsequently dried at 40° C. under vacuum and milled, yielding a crystalline GLDA-NaH$_3$ powder. The crystalline powder was compared with amorphous product in a moisture absorption test.

Amorphous GLDA-NaH$_3$

Dissolvine GL-47-S was acidified to a pH of 3.0 using the above-described BPM process.

The solution was spray-dried applying a NIRO A/S MOBILE MINOR$^{tm}$ spray dryer at an inlet temperature of 220° C., an outlet temperature of 115° C., and a spray pressure nozzle (gap=1 mm) of 1 bar.

The hygroscopic properties of the obtained amorphous GLDA-NaH$_3$ powder were compared to the GLDA-NaH$_3$ crystals using a moisture absorption test.

3.498 g GLDA-NaH$_3$ crystals and 6.114 g spray-dried (amorphous) GLDA-NaH$_3$ were weighed in. Both solids were stored at 16° C. and 60% Relative Humidity.

After 52 hours the weight was found to be 3.509 g for the crystalline GLDA-NaH$_3$ and 6.871 g for the amorphous GLDA-NaH$_3$.

The spray dried, amorphous GLDA-NaH$_3$ showed a weight increase of more than ~12 wt %. The crystalline GLDA-NaH$_3$ had a weight increase of only 0.3 wt % and remained stable (no further moisture pick-up).

Figure 4:
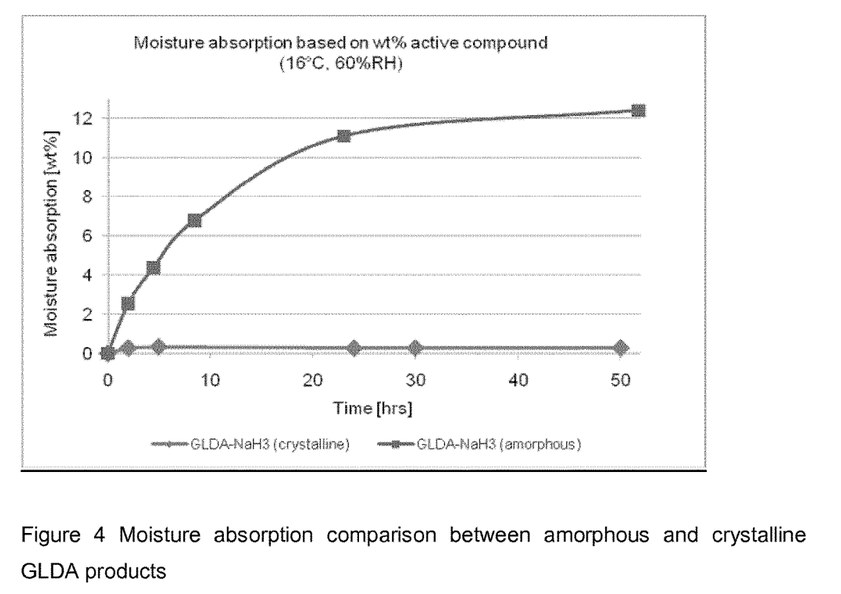
FIG. 4 is a graph illustrating the differences in moisture absorption based on wt% active compound of the amorphous NaH$_3$-GLDA and the crystalline NaH$_3$-GLDA, each as prepared in Example 4.

The comparison between the moisture uptake of amorphous GLDA-NaH$_3$ and the crystalline GLDA-NaH$_3$ as a function of time is shown in FIG. 4. This shows that the crystalline product has significantly reduced hygroscopic properties.

Example 5

Preparation of Crystalline D L-GLDA-NaH with Temperature and Pressure Treatment Step The resulting 44.1 wt % L-GLDA aqueous solution with pH 2.5 (which corresponds to a solution containing about 1 equivalent of sodium cation per GLDA anion) of Example 1 was submitted to a heat and pressure treatment by precharging a 2 L-ss jacketed autoclave provided with a Ruston turbine stirrer with 1.5 l of L-GLDA-NaH$_3$-solution. After inertization of the system with N2-gas, the solution was heated to 135° C. Whilst stirring the temperature was maintained at 135° C., meanwhile the pressure was increased from 2.5 to 2.7 barg. After 3 hours, it was established by monitoring the optical rotation that conversion to a full racemic mixture was completed. After cooling to 70° C. the D,L-GLDA-NaH$_3$ solution was collected in a container.

The obtained D,L-GLDA-NaH$_3$ solution was concentrated to a 50 wt % (50:50) L,D-GLDA-NaH$_3$ aqueous solution in a rotavapor, water bath temperature 70° C. and reduced pressure (20 mbar).

The concentrated solution was charged to a 3 l jacketed glass reactor provided with an anchor stirrer. The aqueous solution was heated to 98° C. for full dissolution. Whilst stirring the clear solution was seeded with GLDA-NaH$_3$ crystals and cooled to 30° C. within 15 hours.

The crystal slurry was centrifuged in a horizontal Rousselet drum centrifuge to separate the mother liquor from the solid product.

After separating off the mother liquor, the wet cake was washed, dried under vacuum at 40° C., yielding dry material that was established to be crystalline by XRD.

Comparative Example 6

Reworking EP-0591934 A1-Example 2

Preparation of GLDA-Na$_4$

The reactor was charged with 80.0 g monosodium glutamate (ex Ajinomoto), 400 g demineralized water, and 36.0 g NaHCO$_3$ (ex J.T.Baker). A solution of 104 g monochloro acetic acid (MCA) dissolved in 400 ml demineralized water was cautiously neutralized with 92.4 g NaHCO$_3$. Whilst stirring the MCA sodium solution was combined with the reactor content. The reaction mixture was heated to 74° C. The pH was kept between 9 and 10 by dosing 30 wt % aqueous NaOH. After dosing of 192 g of 30% aqueous NaOH a pH of 9.8 was reached and the reaction mixture was stirred for another hour.

The reaction mixture was analyzed for impurities by Capillary Zone Electrophoresis. The level of impurities was reasonably low (see Table 1 below).

Whilst cooling the reactor content in a water bath of 15° C. concentrated H$_2$SO$_4$ solution was dosed until the pH was 2 as is (pH 1% sol. 2.5). During dosing of sulfuric acid to the reaction mixture strong CO$_2$ gas evolution was observed (CO$_2$ results from the carbonate).

In total 1,340 g of mixture were collected with Fe-TSV of 6.76 wt % expressed as GLDA-NaH$_3$). On the basis of the pH it was concluded that the product contains about one equivalent of sodium per GLDA and is actually the monosodium salt of GLDA. For simplicity's sake it is referred to in the remainder as GLDA-NaH$_3$ or simply as GLDA.

The yield based on mono sodium glutamate intake was 80.6% GLDA-NaH$_3$.

TABLE 1

Composition of the GLDA-Na$_4$ solution

| Component | Wt % |
|---|---|
| IDA-Na$_2$ | <0.05 |
| HO—CH$_2$—COONa | 1.4 |
| GLMA | 2 |
| HCOONa | 0.1 |
| GLDA-Na$_4$ | 8.3 |

Solidification of the GLDA-NaH$_3$

The acidified reaction mixture was split into two parts. One part was stored at ambient temperature. The other part (670 g) was concentrated in vacuo until half the volume was reached and this solution was allowed to crystallize and analyzed by CZE (see Table 2 below). The filtrate was concentrated further until a paste remained. A small amount of acetone was added to the paste and the sample was stored in the refrigerator at 4° C. for a month. After this time the appearance of the sample looked unchanged. The acetone was removed by decanting. After drying the residue in a vacuum oven at 85° C., the product increased in volume and transformed to a foam-like solid. The material was milled applying a blender before being analyzed by NMR, XRD, CZE, HPLC, and titration with FeCl$_3$ on TSV. The Fe-TSV was determined to be 17.9 wt % expressed as GLDA-H$_4$. By the HPLC analysis the GLDA-NaH$_3$ content was determined to be 15.8±1.5%.

TABLE 2

CZE analysis of composition of solution allowed to crystallize

| Component | Wt % |
|---|---|
| GLDA-NaH$_3$ | 12.4 |
| IDA-H$_2$ | <0.1 |
| Glycolic acid | 2.2 |
| GLMA | 3.2 |
| Formic Acid | 0.2 |
| Na$_2$SO$_4$ | 24.0 |
| NaCl | 8.4 |
| % GLDA on total organic fraction | 69 |
| GLDA:inorganic salt | ~1:2.6 |

To prove the presence of GLDA-NaH$_3$ in the dry solid the product was analyzed by NMR and it was confirmed that the sample still contained a lot of salt and other organic material, as indicated in Table 3 below.

TABLE 3

Chemical composition of organics by NMR of the obtained solid

| Compound | Wt % |
|---|---|
| GLDA-NaH$_3$ | 13.8 |
| GLMA | 7.35 |
| Glycolic acid | 0.10 |

Finally, the solid material was submitted to XRD analysis. Also a XRD diffractogram was taken of D,L-GLDA-NaH$_3$ (as prepared in above Examples 2 and 5). Comparing the diffractograms it must be concluded that the sample does not contain crystalline GLDA. It can be established that the main component in the product is NaCl with a crystallinity of 37%.

Reworking patent EP591934A1—Synthesis Example 2 showed that it is possible to prepare GLDA solution with 74.4% yield based on mono sodium glutamate intake. However, after the addition of the sulfuric acid it was no longer possible to work analogous to the procedure described in the patent. For example, no white powder was formed. Analysis of the products that were obtained demonstrated there was no formation of crystals of GLDA sodium salt. This confirms that sodium GLDA will only crystallize after a racemization step that causes the compound to at least partially racemize. Also, the high amount of salt will have had an inhibiting influence on the crystallization of the organic GLDA material.

The invention claimed is:

1. Salt of glutamic acid-N,N-diacetic acid (GLDA) of the formula GLDA-Y$_m$H$_n$, wherein m is equal to or more than 0.5 and lower than or equal to 2.5, n+m=4, and wherein Y is a monovalent cation that is not a proton, comprising L-GLDA-$Y_mH_n$ to D-GLDA-$Y_mH_n$ in a range between 100:0 and 50:50 (L:D), characterized in that the salt is crystalline.

2. Salt of the formula GLDA-$Y_mH_n$ according to claim 1, wherein Y is an alkali metal.

3. Salt of the formula GLDA-$Y_mH_n$ according to claim 1, wherein m is about 1 and n is about 3.

4. Salt of the formula GLDA-$Y_mH_n$ according to claim 1, wherein the salt comprises L-GLDA-$Y_mH_n$: D-GLDA-$Y_mH_n$ between 75:25 and 50:50 (L:D).

5. Process to prepare the salt of the formula GLDA-$Y_mH_n$ according to claim 1, comprising:
- a first step providing an aqueous solution containing a salt of GLDA and/or GLDA-$H_4$,
- a second step ensuring that the pH of the aqueous solution is equal to or more than 1.8 and less than 5 and performing a racemization step to at least partially racemize the salt of GLDA, one step after the other in random order or simultaneously, and
- a third step allowing the aqueous solution to crystallize.

6. Process according to claim 5, wherein the pH of the second step is in the range between 1.8 and 4.8.

7. Process according to claim 5, wherein the second step includes a concentrating step.

8. Process according to claim 7, wherein the concentrating step is carried out until the solution has a concentration of equal to or more than 15 wt % up to or equal to 80 wt %, of GLDA-$Y_mH_n$ based on the weight of the aqueous solution.

9. Process according to claim 5, wherein the third step comprises crystallization accomplished by a step selected from the group consisting of allowing the solution to stand until the solution crystallizes, cooling, and seeding.

10. Process according to claim 5, wherein the third step comprises spraying the aqueous solution of the second step on seeding crystals.

11. Process according to claim 5, wherein the third step is performed at a temperature of equal to or below 30° C.

12. Process according to claim 5, wherein the process is a continuous process.

13. Process according to claim 5, comprising an additional step wherein carbonates, silicates, or a combination of carbonates and silicates are added to the resulting product of the third step, so that the pH of an aqueous solution of the resulting product is above 6.

14. Detergent compositions containing the salt of the formula GLDA-$Y_mH_n$ according to claim 1, and further comprising at least one component selected from the group consisting of cleaning additives, antiscaling additives, builders, protective colloids, chelating agents, surfactants, corrosion inhibitors, and inorganic or organic acids.

15. Pharmaceutical preparations containing the salt of the formula GLDA-$Y_mH_n$ according to claim 1, and further comprising a pharmaceutically acceptable carrier.

* * * * *